United States Patent
Feng et al.

(10) Patent No.: US 12,214,216 B1
(45) Date of Patent: Feb. 4, 2025

(54) PHOTON ENHANCED BONE GROWTH SYSTEM AND METHOD

(71) Applicants: Helen Feng, Palo Alto, CA (US); Weiping Wang, Palo Alto, CA (US)

(72) Inventors: Helen Feng, Palo Alto, CA (US); Weiping Wang, Palo Alto, CA (US)

( * ) Notice: Subject to any disclaimer, the term of this patent is extended or adjusted under 35 U.S.C. 154(b) by 0 days.

(21) Appl. No.: 18/401,209

(22) Filed: Dec. 29, 2023

Related U.S. Application Data

(63) Continuation-in-part of application No. 17/071,994, filed on Oct. 15, 2020, now abandoned.

(60) Provisional application No. 62/916,078, filed on Oct. 16, 2019.

(51) Int. Cl.
*A61N 5/06* (2006.01)
*A61N 5/04* (2006.01)

(52) U.S. Cl.
CPC .............. *A61N 5/062* (2013.01); *A61N 5/04* (2013.01); *A61N 2005/066* (2013.01); *A61N 2005/0663* (2013.01)

(58) Field of Classification Search
CPC ..... A61N 5/062; A61N 5/04; A61N 2005/066
See application file for complete search history.

(56) References Cited

U.S. PATENT DOCUMENTS

| | | | |
|---|---|---|---|
| 11,865,356 B1* | 1/2024 | Vorwaller | A61N 5/06 |
| 2004/0170626 A1 | 9/2004 | Schuurman | |
| 2010/0029709 A1 | 2/2010 | Menet | |
| 2016/0016001 A1 | 1/2016 | Loupis | |
| 2018/0066046 A1 | 3/2018 | Smith | |
| 2018/0305450 A1 | 10/2018 | Dobson | |
| 2019/0091138 A1* | 3/2019 | Hattersley | A61P 43/00 |

OTHER PUBLICATIONS

Swanson et al, "The importance of the circadian system and sleep for bone health", 2017, Metabolism Clinical and Experimental (Year: 2017).*

(Continued)

*Primary Examiner* — Lynsey C Eiseman
*Assistant Examiner* — Jessica L Mullins
(74) *Attorney, Agent, or Firm* — ROARK IP

(57) ABSTRACT

The present disclosure relates generally to a therapeutic system and method to manage and modulate inflammation by reducing inflammation with enhanced anti-inflammatory measures. Using a light source such as light emitting diodes (LEDs) or a laser light source, the photons can be used to applied to increase the efficacy of medicine on the organ (i.e., disease site) that needs treatment by imparting the light rays only to the site rather than the whole body. The photons produced by the light source increase adenosine triphosphate (ATP) to improve the functional selectivity of G Protein-Coupled Receptors (GPCR). With the increased efficacy of medicines to the disease site, the dosage of medicine can be reduced to minimize the side effects in particular to other parts of the body. The treatment may be used to treat inflammation caused by corona virus of 2019 (COVID-19) infection. The photon irradiation treatment can be used to enhance bone growth with parathyroid hormone (PTH) and parathyroid hormone-related protein (PTHrP).

14 Claims, 11 Drawing Sheets

(56) References Cited

OTHER PUBLICATIONS

Tafur J, Mills PJ. Low-intensity light therapy: exploring the role of redox mechanisms. Photomed Laser Surg. Aug. 2008;26(4):323-8.
Arno Wiehe, "Trends and targets in antiviral phototherapy" Photochem. Photobiol. Sci., 2019, 18, 2565-2612 (Year: 2019) (Year: 2019).
Devnani, "Phototherapy: Role in Sleep Disorder", Indian Journal of Sleep Medicine, p. 1-6, 2014.
Maul, "Impact of UVA On Pruritis During UVA-B/Phototherapy of Inflammatory Skin Diseases . . . ", University of Zurich, 2017.

\* cited by examiner

F\G. 4

PHOTON ENHANCED BONE GROWTH SYSTEM AND METHOD

PRIORITY CLAIM

This patent application claims the benefit of U.S. patent application Ser. No. 17/071,994, filed on Oct. 15, 2020; which claims the benefit of U.S. Provisional Patent Application Ser. No. 62/916,078, filed Oct. 16, 2019; the aforementioned applications being incorporated herein by reference in their entireties.

FIELD OF THE DISCLOSURE

The present disclosure relates generally to a therapeutic tool and method to manage and modulate inflammation by reducing inflammation with enhanced anti-inflammatory measures. The tool and method amplifies the effects of therapeutic targets of G protein-coupled receptors including parathyroid hormone, parathyroid hormone-related protein and others.

BACKGROUND

Phototherapy is also used for certain cosmetic dermatological conditions. Procedures to remove unwanted hair, remove vascular lesions or pigmentation, eliminate acne, and rejuvenate the skin, for example, are becoming common. These treatments typically use light in either ultraviolet light. Common devices for these treatments are lasers; however, other light sources, including LED's, are also available for certain of these treatments like acne.

SUMMARY

Aspects of the disclosure include: a method for treating inflammation comprising: apply a light with a predetermined energy and a predetermined time to an organ in a human body; and treat with a nonsteroidal anti-inflammatory drug (NSAID) medicine.

Aspects of the disclosure further include: a method for treating inflammation comprising: apply a light with a predetermined energy and a predetermined time to an organ in a human body; and treat with a glucocorticoid (GC).

Aspects of the disclosure further include: a method for treating inflammation comprising: apply a light with a predetermined energy and a predetermined time to an organ in a human body and treat with an anti-metabolite.

Aspects of the disclosure further include: a method for treating inflammation comprising: apply a light with a predetermined energy and a predetermined time to an organ in a human body and treat with at least one medicine from the group consisting of: molecules that bind to G protein-coupled receptors (GPCRs), a nonsteroidal anti-inflammatory drug (NSAID), a glucocorticoid, an anti-metabolite, a biologic immunomodulator, and bone growth agents.

DETAILED DESCRIPTION

Although particular aspects or features of the following disclosure may be described with reference to one or more particular embodiments and/or drawings, it should be understood that such features are not limited to usage in the one or more particular embodiments or drawings with reference to which they are described, unless expressly specified otherwise. The functionality and/or the features of the embodiments that are described may be alternatively embodied by one or more other devices which are described but are not explicitly described as having such functionality/features.

Inflammation by immune cells is human body's natural response to defend infection of foreign pathogens (i.e., pathogen associated molecular pattern (PAMPs) molecules), such as bacteria or virus. They are also responsible for repairing body damages from injuries (i.e., damage associated molecular patterns (DAMPs). However, prolonged inflammations are known to causing body damages in many chronic diseases including atherosclerosis, rheumatoid arthritis, osteoarthritis, osteoporosis, psoriatic arthritis, ankylosing spondylitis, fibromyalgia, psoriasis, chronic obstructive pulmonary disease, obesity, cancer, multiple sclerosis, asthma, and gout. These chronic diseases in general have no known cure to-date, causing high economic cost to society. In addition, genetic variation of human genome is a cause of individuals' responses to medications. Some individuals are less responsive to medication and some individuals are less tolerating to side effects. Thus a method to improve efficacy and/or to reduce adverse reactions and side effects is needed. The present disclosure relates generally to a therapeutic tool and method to manage and modulate inflammation by suppressing pro-inflammatory mechanisms or improving timely resolution of inflammation with enhanced anti-inflammatory measures.

Figure 1:
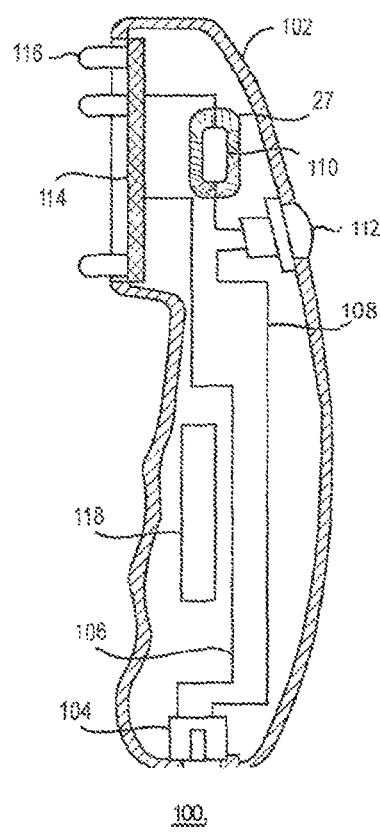
FIG. 1 shows a cross sectional view of a handheld version of a Light Emitting Diode (LED) light therapy device 100.

FIG. 1 shows a cross sectional view of a Light Emitting Diode (LED) light therapy device 100. Device 100 can be handheld or attached to a fixture, a multi-joint mechanical linkage, or a computer controlled manipulator such as a robotic arm for positioning and orienting in a three-dimensional space. The device 100 includes an array of light emitting diodes incorporated in 9-18 parallel circuits of 4 in a series of conventional light emitting diodes configured to emanate a selectable distribution of light in the following wavelengths 460 nm, 605 nm, 630 nm, 660 nm, 850 nm and 940 nm, depending on the configured intent of the device 100. The selection for the different wavelength light emitting diodes based upon the intended use. While a particular number and array of light emitting diodes has been disclosed more or less light-emitting diodes can be used in other larger or smaller designs.

In FIG. 1 the device 100 is enclosed in a plastic or metal housing 102. The device 100 is energized by a power source which can be a battery or an alternating current (AC)-to-direct current (DC) converter through a connector 104 to a negative lead 106 and a positive lead 108. The power goes through a power controller 110 then to the on/off switch 112 and finally to the rigid printed circuit board 114 that holds the different wavelength light emitting diodes 116. A weight 118 is preferably placed in the handle to provide balance to the device. A power controller 110 controls the duration of pulse, frequency, and amplitude of voltage for effecting the intensity and duration of the treatment LED. The device is 110 also thermally enclosed, jacketed or otherwise covered to further disperse any heat away from the treatment area. Although LED is a preferred light source, alternatively laser can be used.

FIG. 1 comprises a cross sectional view through the device 100 including a printed circuit board 114 having light emitting diodes 116. (In alternative embodiments, the LEDs 116 may be replaced with a laser). The output of all of the light emitting diodes 116 is directed outward at right angles, or normal, to the circuit board 118 on which they are mounted without lenses, mirrors, reflective surfaces, optical systems or any intermediary material.

Figures 2, 3:
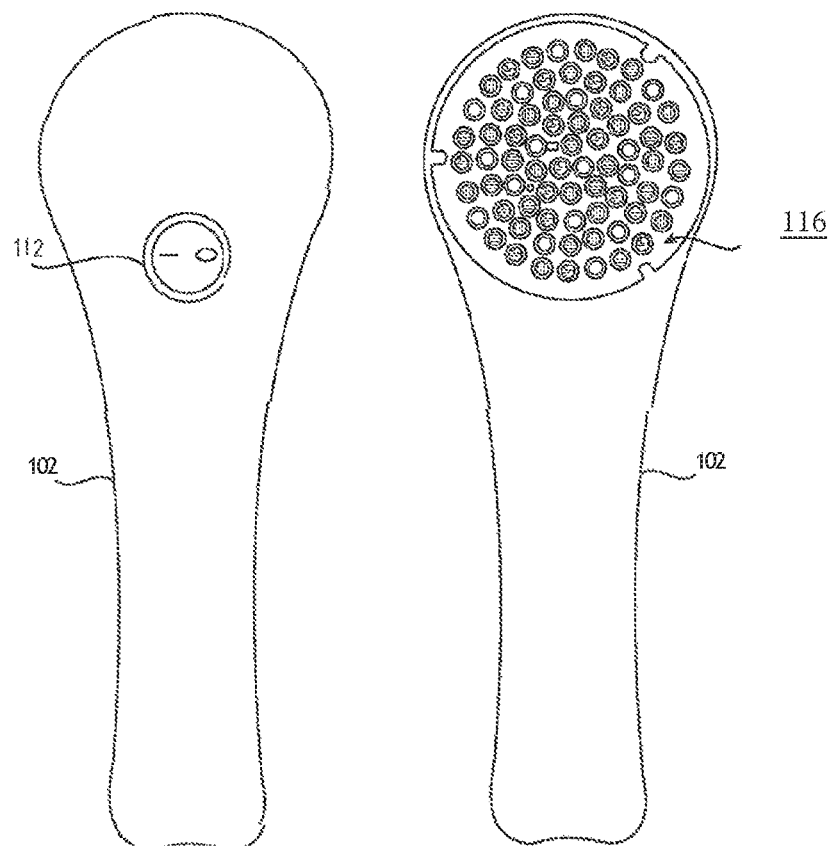
FIG. 2 and FIG. 3 show a top view and bottom view, respectively, of the device 100 showing the location of the on/off power switch 16 and an arrangement of the light emitting diodes 116 arranged for multiple purposes in the housing 102.

FIG. 2 and FIG. 3 show a top view and bottom view, respectively, of the device showing the location of the on/off power switch 16 and an arrangement of the light emitting diodes 116 arranged for multiple purposes in the housing 102.

Figure 4:
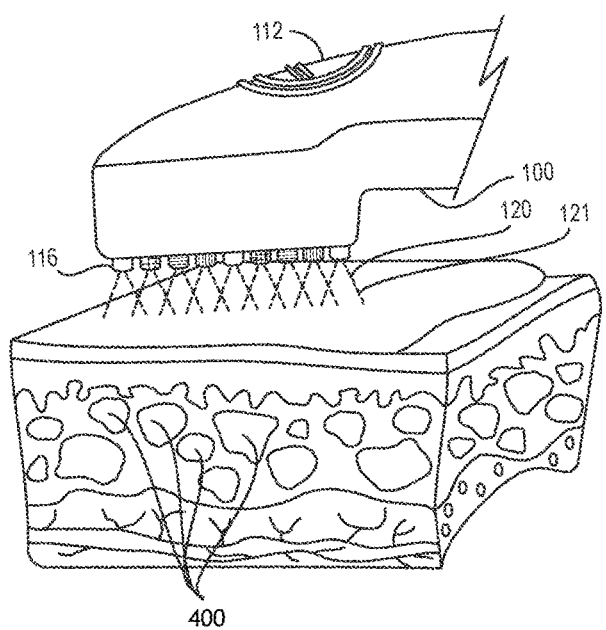
FIG. 4 shows the device 100 in use with cells 400.

FIG. 4 shows the device 100 in use with cells 400. LED light therapy is the use of specific types of light that give off energy that stimulates cells 400. The light emitting diodes 116 give off energy in the form of light rays 120 having photons 121. The light emitting diodes 116 are compact, durable, powerful, bright, efficient, and produce effects on the cells. Device 100 translates energy in a manner similar to the process of plant photosynthesis into the workings of human cells. With light emitting diodes 116, the correct wavelengths of light can closely penetrate into the body to act on cells at desired depths and intensities.

Figure 5:
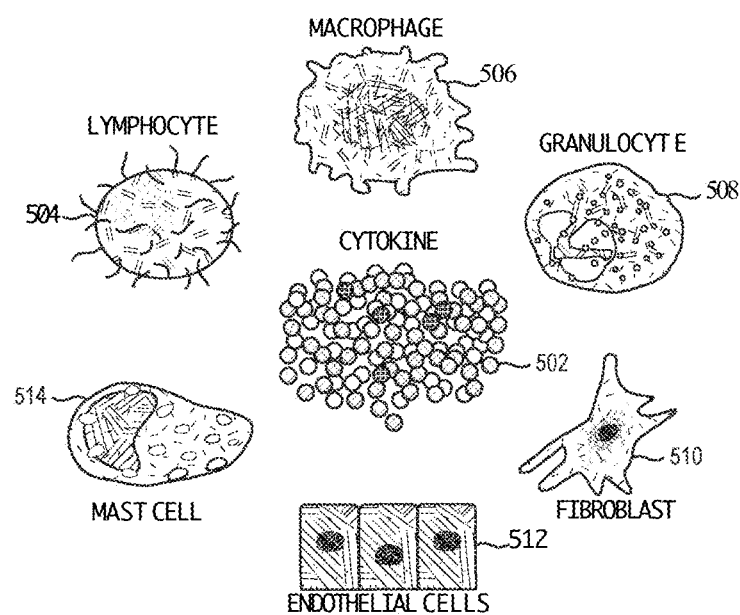
FIG. 5 shows various immune cells can release and can be stimulated by cytokines 502.

FIG. 5 shows an immune system 500 evolved to protect the host from invading foreign pathogens, allergens and different xenobiotics. The system 500 comprises both cellular and humoral components such as cytokines 502 secreted by immune cells. In order to mount and coordinate an effective immune response, a mechanism by which lymphocytes 504, inflammatory cells and hematopoietic cells can communicate with each other is required. Cytokines 502 perform this function. Cytokines are a large, diverse family of small proteins. The immune cells may comprise lymphocytes 504, macrophages 506, granulocytes 508, fibroblasts 510, endothelial cells (ECs) 512, and mast cells 514. Cytokines can also activate adaptive immune lymphocytes 504 including B cells, killer T cells and helper T cells. Influencing both innate and adaptive immune responses, the two principal producers of cytokines are helper T cells (Th cells) and macrophages 506, although they can be transiently induced and secreted by virtually all nucleated cells. Inflammation by immune cells are human body's natural response to defend infection of foreign pathogen associated molecular patterns (PAMPs) such as bacteria or virus. They are also responsible for repairing body damages from injuries such as damage associated molecular patterns (DAMPs). Once pathogens are eliminated and damages are repaired, the immune system's responses and inflammation should subside. However, due to pathological conditions such as cytokine dysregulation or autoimmune, as well as aging, cytokine expression and prolonged inflammations can persist and become destructive. Prolonged inflammation and overactive inflammation are known to cause damages to cardiovascular, neural, pulmonary, gastrointestinal, dermatological, renal, musculoskeletal systems or other organs in the body. This disclosure includes a new therapeutic tool and method using photons to synergistically enhance the therapeutic effect of medications for disorders including but not limited to musculoskeletal inflammatory disorders such as osteoarthritis, osteoporosis, rheumatoid arthritis, psoriatic arthritis, ankylosing spondylitis and gout. Dermatological inflammatory disorders also may be treated such as acne, dermatitis, cellulitis, eczema, psoriasis, skin ulcer and alopecia.

Figure 6:
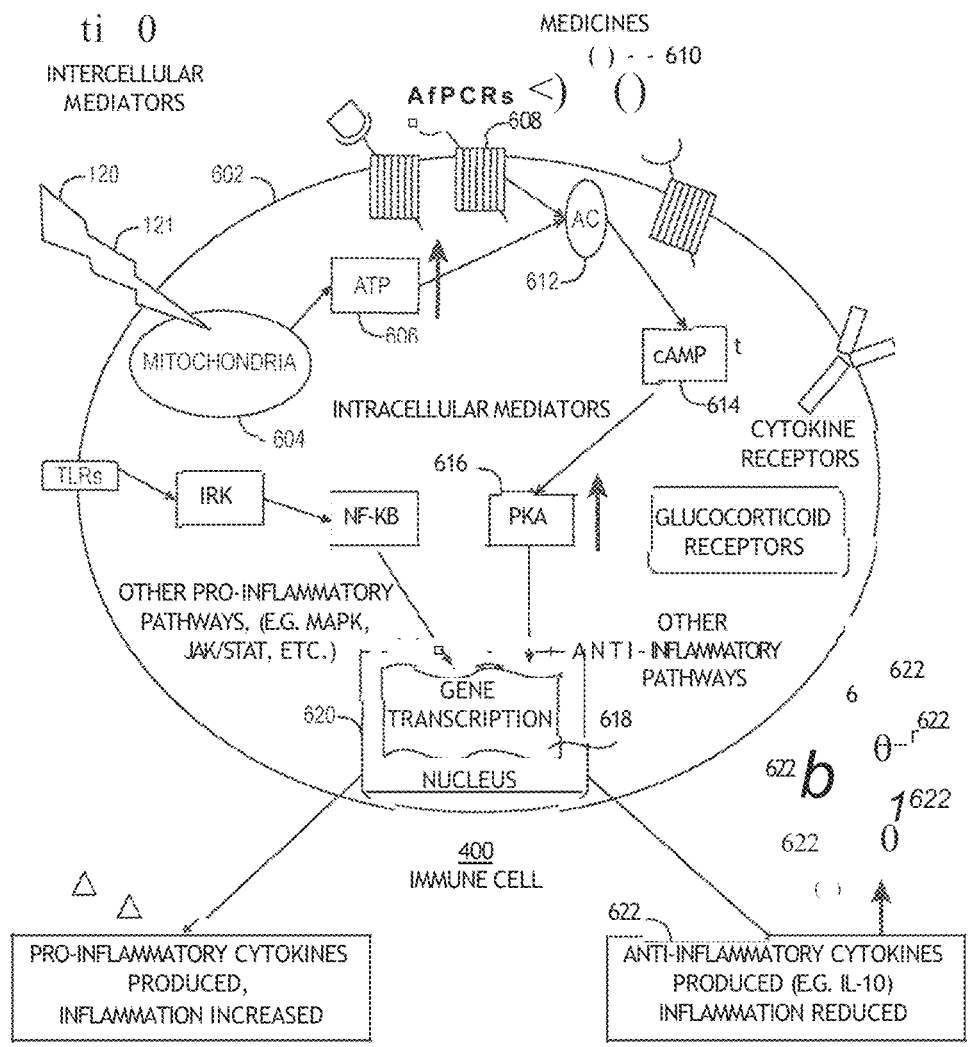
FIG. 6 shows a detailed view of a cell 400 having a cell membrane 602.

FIG. 6 shows a detailed view of a human cell 400 having a cell membrane 602. Photons in light rays 120 activate mitochondria 604 in the cell 400. Mitochondria 604 are responsible for converting nutrients into an energy carrier known scientifically as adenosine triphosphate (ATP) 606. ATPs 606 fuel the cell's 400 activities. The ATP 606 gives the cell 400 the needed energy to do their job. This is the reason mitochondria 604 are frequently referred to as the powerhouse of the cell 400. The light rays 120 sent by the device 100 into the cell 400 excites the mitochondria 604 into producing in some cases up to 10 times more ATP, although usually 2 to 4 times.

G protein-coupled protein receptors (GPCRs) 608 are targets of various drugs (or medicines). Drugs may be administered by intravenous infusion, injection (e.g., subcutaneous injection), orally, by inhalation, or topically applied. GPCRs are a family of transmembrane proteins which detect molecules 610 (e.g., medicines) outside the cell 400 and passes on signals into the cell 400 that produces responses. There are about 1000 drugs that are known to act on over 100 unique GPCRs. The medicine 610 may be nonsteroidal anti-inflammatory drugs (NSAIDs) or steroids. Steroid hormones may include sex hormones (which influence sex differences and support reproduction), corticosteroids (which include most synthetic steroid drugs, glucocorticoids (which regulate many aspects of metabolism and immune function) and mineralocorticoids (which help maintain blood volume and control renal excretion of electrolytes), and anabolic steroids (which interact with androgen receptors to increase muscle and bone synthesis). Upon the binding of GPCRs with medicine outside the cell, a subunit of G protein can be activated to interact with proteins such as adenylyl cyclase (AC) 612 inside the cell. Adenylyl cyclase (AC) 612 catalyzes adenosine triphosphate (ATP) 606 into cyclic adenosine monophosphate (cAMP) 614. cAMP 614 is an intracellular second messenger relating extracellular signals from GPCRs to key mediators such as protein kinase A (PKA) 616 within the cell. PKA 616 activates gene transcription 618 in nucleus 620 to release anti-inflammatory cytokines 622 to help maintain the homeostasis of immune system.

Figure 7:
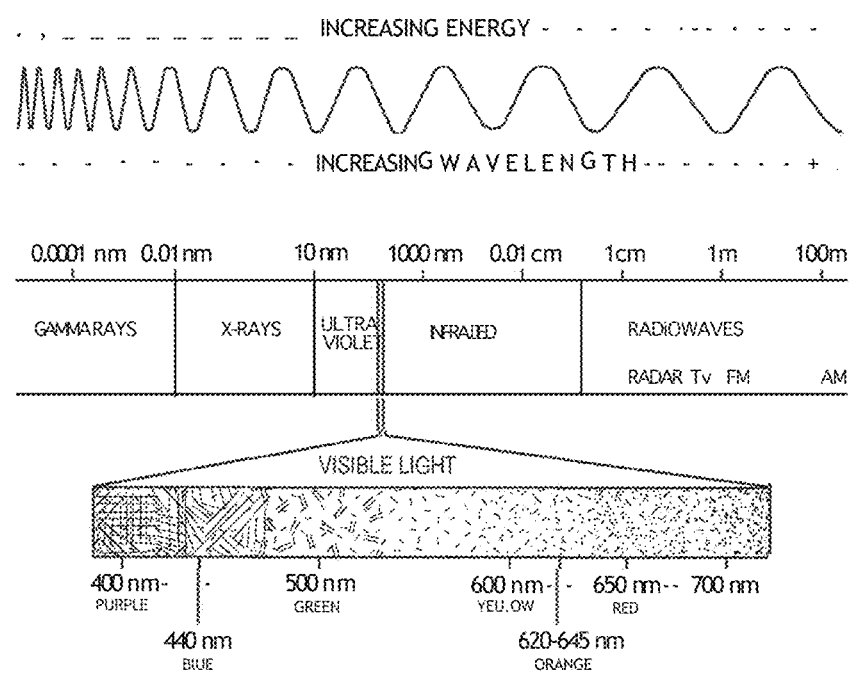
FIG. 7 shows the energy E of a photon 121 is characterized by $E=h\upsilon$ which is the multiplication of Planck's constant (h) by the frequency ($\upsilon$) of the light rays 120

Referring to FIG. 7, the energy E of a photon 121 is characterized by $E=h\upsilon$ which is the multiplication of Planck's constant (h) by the frequency ($\upsilon$) of the light rays 120. Photons 121 may range from 100 nanometers (nm) to 1000 nm to stimulate the cell 400 which includes visible light spectrum and certain ultraviolet (UV) and infrared bands. The photons 121 can be one or more narrow bands of light generated by device 100. The penetration by light into the body is inversely related to light wave frequency. Lower frequency light penetrates deeper. Based on the range of depth where the targeted cells, tissues, and organs are located, suitable bands of light can be selected for higher efficiency.

Figure 8:
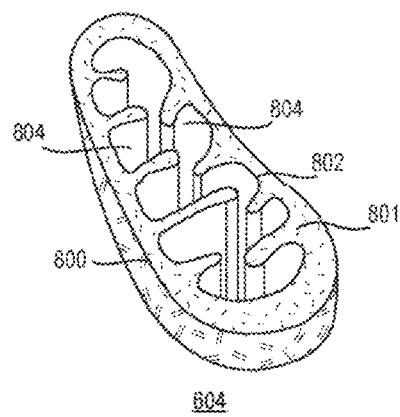
FIG. 8 shows an enlarged perspective view of the cross-section of mitochondria 604.

FIG. 8 shows an enlarged perspective view of a mitochondria cell 604. The mitochondria 604 has an outer membrane 800, an intermembrane space 801 and an inner membrane 802. Cristae 804 are each of the partial partitions in a mitochondrion 604 formed by infolding of the inner membrane 802.

Figure 9:
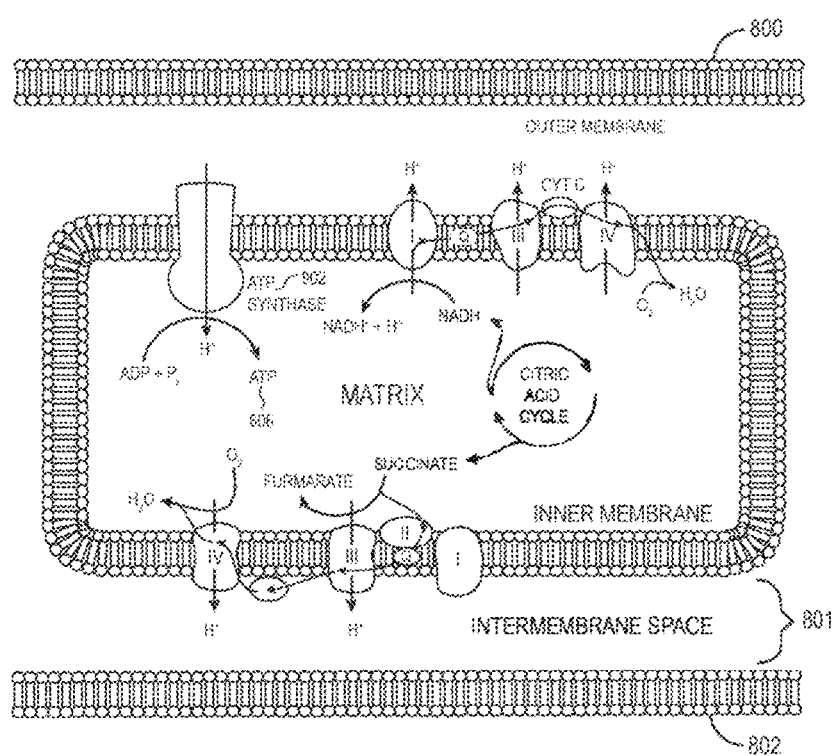
FIG. 9 shows a detailed view of the mitochondria inner membrane and intermembrane space 801.

FIG. 9 shows a detailed view of the intermembrane space 801. ATP 606 is produced in the ATP syntase complex (also known as complex IV) 902 of mitochondria 604. The production of ATPs 606 can be increased with the energy from photons 121 in selective bands of wavelengths within or near visible light spectrum such as red and infra-red. The increased ATP 606 can up-regulate the cAMP 614 and PKA 616 to activate gene transcription for more anti-inflammatory cytokines 622 amplifying the intended effect of anti-inflammatory medication received by GPCRs.

Medicines 610 such as steroids or nonsteroidal anti-inflammatory drugs (NSAIDs) are the most commonly used medicines in inflammatory diseases since they are effective in management of pain, fever, redness, edema, and joint stiffness arising as a consequence of inflammatory cytokines 622 being released. NSAIDs may include acetylsalicylic acid (aspirin), celecoxib, diclofenac, diflunisal, etodolac, ibuprofen, indomethacin, ketoprofen, and naproxen. These NSAIDs control inflammation mainly by inhibiting the cyclooxygenase (COX)—an enzyme to produce prostaglandins. Aspirin, a COX-1 inhibitor, is associated with a number of adverse side effects including gastrointestinal erosions and renal and hepatic insufficiency. The side effects of celecoxib, a COX-2 inhibitor, may include insomnia, abdominal pain, flatulence (gas), headache, nausea, diarrhea, and pharyngitis. Notably, rofecoxib is a COX-2 inhibitor for treating osteoarthritis, osteoporosis, rheumatoid arthritis, juvenile rheumatoid arthritis, acute pains, migraine, and dysmenorrheal. Rofecoxib was withdrawn from the market due to elevated cardiovascular risk of heart attack. NSAIDs as a class of anti-inflammatory drug have broad side effects, due to inhibition of the broad functions of COX to various cells and organs in the body. Common side effects and adverse reactions of most NSAIDs include upset stomach, headache, dizziness, drowsiness, rash, and ringing in the ears. Further enumeration of side effects can be found in the literatures from the manufactures of respective dugs and are not listed herein. NSAIDs will typically also reduce the ability of blood to clot and therefore increase bleeding after an injury.

Photons 121 applied by device 100 can be used on a target area of the body in conjunction with a variety of medicines 610 so as to selectively increase the efficacy and to reduce the side effects of medicines 610 to other functions or others organs of the body. The medicines 610 may also be another class of anti-inflammatory drugs including glucocorticoids (GC), anti-metabolites, and biologic immunomodulators. Glucocorticoids such as betamethasone and methylprednisolone acetate are a class of broad action steroids for treating many general inflammations as well as osteoarthritis and gout. It bonds to the glucocorticoids receptor to regulate various cardiovascular, metabolic, immunologic, and homeostatic functions. Anti-metabolites such as methotrexate can mediate folate pathways and nucleotide biosynthesis to reduce the inflammation for rheumatoid arthritis, psoriasis, psoriatic arthritis and other autoimmune diseases. Biologic immunomodulators such as tumor necrosis factor-α (TNF-α) inhibitors, interleukin-6 (IL-6) inhibitors, interleukin-17 (IL-17) inhibitors and janus kinase (JAK) inhibitors block overproduction of said cytokines respectively, which are signaling proteins involved in rheumatoid arthritis, psoriasis, psoriatic arthritis and other inflammatory diseases. These medicines are powerful anti-inflammatory with systemic actions. So improving the selectivity of these medicines usage with light applications locally is beneficial in reducing side effects. The medicines can be applied using either intravenous infusion, subcutaneous injection, oral, or topical. With photo enhancement, dosages of medication 610 may be reduced and thus reduced side effects and adverse reactions but still being able to maintain or to increase the effectiveness of medicines.

Using LEDs 116 (or a laser light source), the photons 121 can be applied to increase the efficacy of medicine 610 on the organ (i.e., disease site) that needs treatment by imparting the light rays 120 only to the site, rather than the whole body. The photons 121 increase ATP 606 to improve the functional selectivity of GPCR 608. For activating typical musculoskeletal and dermatological cells for enhancing medication, light comprising approximately 30% to 70% (e.g., 50%) of 660 nanometers (nm) wavelength light waves from red LED and the remainder in the range of 70% to 30% correspondingly (e.g., 50%) in 850 nm wavelength light waves from infra-red LED can be used. The irradiation energy may be approximately 30 to 150 joules per square centimeter ($J/cm^2$) treatment area. The light can be applied for approximately 10 to 30 minutes per day using LED's of a predetermined power rating. With the increased efficacy of medicines to the disease site, the dosage of medicine can be reduced to minimize the side effects, in particular to other parts of the body. In alternative embodiments, the device 100 may have a projective lens attached to the LEDs 116 or laser light source to increase the focusing ability of the light rays 120. Photons 121 may be used according to the circadian rhythms of the inflammatory pathways (i.e., mediators) to optimize the efficacy of medicine 610.

Pre-medicine treatment of the organ may be used to treat chronic inflammation, chronic inflammation-related diseases, and/or non-subsiding acute inflammation. In a first step, light therapy is applied to the organ. In a second step, medicine is applied. The first step and second steps may be applied simultaneously or in an opposite order. The light stimulates mitochondria and the medicine stimulates GPCRs. ATP generation is increased as well as cAMP and PKA also being increased. PKA promotes gene transcription of anti-inflammatory measures including producing anti-inflammatory cytokines to reduce the inflammation. As a result, an inflammatory response is reduced and/or resolved.

Coronavirus disease of 2019 (COVID-19) patients could develop various kind of post-viral musculoskeletal inflammations such as arthritis, joint pains, muscle ache, as well as vascular inflammation such as purple toes (ie., capillary blood clots). This may be due to the fact that COVID-19 virus or injuries caused by COVID-19 virus is not completely cleared from the body.

Bone remodeling is an ongoing process by which old bone is replaced by new bones. Osteoporosis, a condition frequently associated with aging, is characterized by diminished bone mass, compromised bone strength, and impaired bone quality. This condition arises from an imbalance between the resorption carried out by osteoclasts and the formation facilitated by osteoblasts, resulting in a net loss of bone mass and microstructure. Consequently, individuals with osteoporosis face an elevated risk of fractures.

Proteins comprises of parathyroid hormone (PTH) and parathyroid hormone-related protein (PTHrP) have been used in helping bone formation. Teriparatide is a recombinant PTH analog. It is made up of the first amino (N)-terminal 34 amino acids of the human. Teriparatide's chemical name is Human Parathyroid Hormone Fragment (1-34) and its chemical formula is $C_{63}H_{88}N_{14}O_{14}$. Abaloparatide is a 34 amino acid synthetic analog of human PTHrP. Abaloparatide's chemical name is [Glu1, Nle18, Tyr34]-hPTH (1-34), and its chemical formula is $C_{174}H_{282}N_{50}O_{49}$. Pharmacologically, both teriparatide and abaloparatide can be used for treating osteoporosis by promoting bone growth and increasing bone mass density (BMD). However, the treatment for bone growth with either teriparatide or abaloparatide is recognized as a gradual, slow process, necessitating an extended duration of therapy. For instance, teriparatide exhibits noticeable effects only in the second year of treatment, and abaloparatide requires 24 weeks and more to manifest an increase in BMD. Therefore, there is a need for a method to expedite the rate of BMD improvement in osteoporosis.

Due to the protracted nature of bone remodeling, the therapeutic regimen of abaloparatide is typically a daily injection over a duration of 1.5 to 2 years. However, insights from animal studies underscore a potential risk of bone cancers associated with heightened dosage or prolonged treatment. Consequently, extending the treatment beyond 2 years for additional BMD gain is not recommended.

In the context of a fractured bone, the healing process is an intricate biological response to restore the bone's original structures and biomechanical functions. In conventional treatment, specialized implants like plates, screws, nails, and wires are employed to secure the fractured bone until it attains sufficient strength to withstand the body's weight and movement. These implants are surgically inserted to offer mechanical support, reducing the likelihood of nonunion (improper healing). Typically, following the surgery to stabilize the fractured bone, the bone is anticipated to undergo self-repair with minimal medical interventions.

For the repair of a fractured bone, various biological processes encompassing inflammation, signaling, gene expression, cellular proliferation, differentiation, osteogenesis, chondrogenesis, angiogenesis, and remodeling take place in the bone. The physiological bone repair unfolds through several stages:

1. Inflammatory Phase (1-2 weeks): Immediately following a fracture, the body initiates an inflammatory response to minimize bleeding, eliminate debris, and counteract bacteria.
2. Reparative Phase (2 weeks to several months): This phase involves the creation of a soft callus comprised of cartilage, providing initial stability. Subsequently, osteoblasts replace the soft callus with a hard callus made of woven bone through a process known as ossification.
3. Bone Remodeling Phase (several months to years): Osteoclasts remove excess bone, and osteoblasts deposit new compact bone until the bone regains its original shape and strength.

In general, the healing duration for a fractured bone is extensive, spanning from several months to years, influenced by factors like the type of injury, individual health conditions, and age. Notably, fractured bones in older adults exhibit a slower healing process. Consequently, there is a need for methods to expedite bone growth in healing of fractured bones.

When expediting bone growth, two key bottlenecks in the signal pathway for osteoblasts must be addressed: (1) the ligand binding to the G protein-coupled receptor (GPCR) on the cell membrane and (2) the intracellular second messenger activating gene transcription in the nucleus. In one embodiment, the resolution of bottleneck (1) involves the administration of either teriparatide or abaloparatide, while the alleviation of bottleneck (2) is achieved through the synergistic application of photon irradiation—comprising both red light and infrared (red/IR) light—to accelerate bone remodeling and growth. At the core of red and IR photon irradiation's mechanism of action lies an augmentation in increased ATP production by mitochondria, as detailed in preceding sections.

Figure 10:
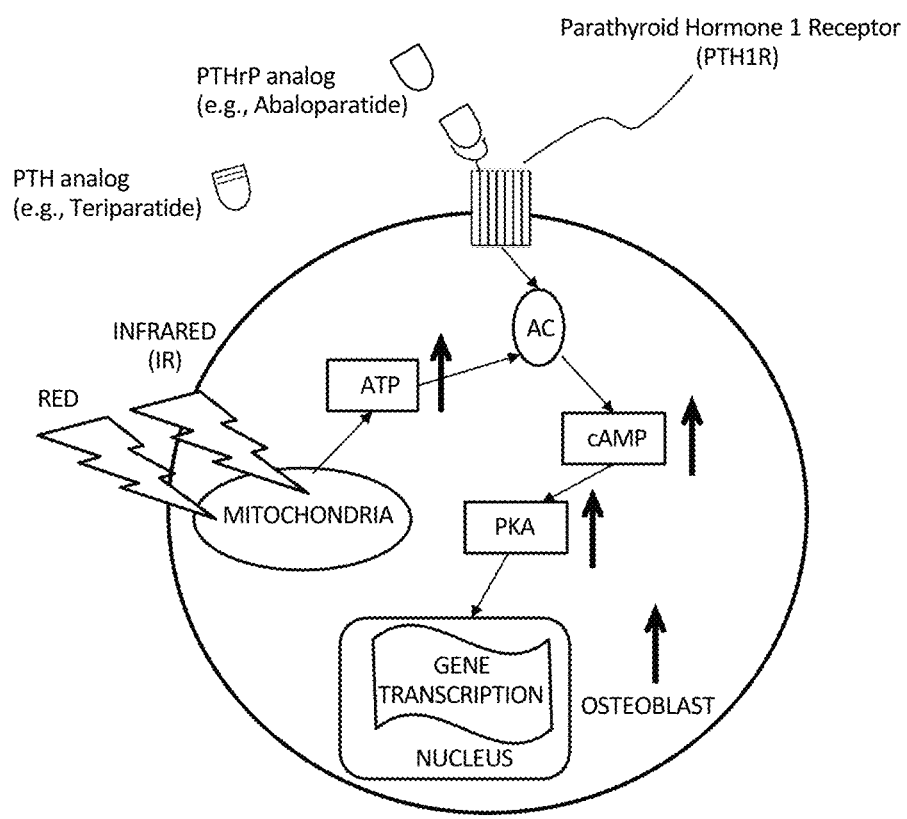
FIG. 10 shows a therapeutic pathway targeted by either teriparatide or abaloparatide with photon enhanced activation of gene transcription for osteoblast.

FIG. 10 illustrates parathyroid hormone 1 receptors (PTH1R), a subtype of G protein-coupled receptor (GPCR), situated on the cell membrane of osteoblasts. PTH1R binds to ligands such as parathyroid hormone (PTH) or parathyroid hormone-related protein (PTHrP). PTH1R is a key regulator which plays a critical role in maintaining calcium homeostasis and bone turnover. Its function is critical for human health to maintain homeostatic control of ionized serum $Ca^{2+}$ levels and has several signaling features including endosomal cAMP signaling.

PTH1R can be activated through binding of teriparatide (a PTH analog) or abaloparatide (a PTHrP analog). The binding leads to the stimulation of cyclic adenosine monophosphate (cAMP) production. The cAMP signaling pathway is pivotal in the context of bone formation, favoring bone growth through the activation of osteoblasts responsible for synthesizing and depositing new bone matrix. The cAMP-induced activation of protein kinase A (PKA) plays a crucial role. Following activation by cAMP, PKA phosphorylates various target proteins, influencing gene expression essential for bone formation, including proteins involved in synthesizing bone matrix components such as collagen and osteocalcin. Pharmacologically, an analog of PTH (e.g., teriparatide) or an analog of PTHrP (e.g., abaloparitide) can generate born formation when administered by once-a-day injection. But the speed of bone formation using PTH or PTHrP analogs is slow. In one embodiment, the speed of bone formation is increased by red light and IR light irradiation to the site where bone growth is intended. It is noted that cAMP is synthesized from adenosine triphosphate (ATP) by adenylate cyclase, and the cAMP-PKA pathway can be up-regulated and enhanced by red light and IR light photon irradiation. Increased ATP production resulting from red light and IR light photon irradiation amplifies cAMP, consequently enhanced the activation of osteoblasts by either teriparatide or abaloparatide.

Figure 11:
FIG. 11 depicts an magnet resonance (MR) image of knee fracture of a female patient.
Figure 12:
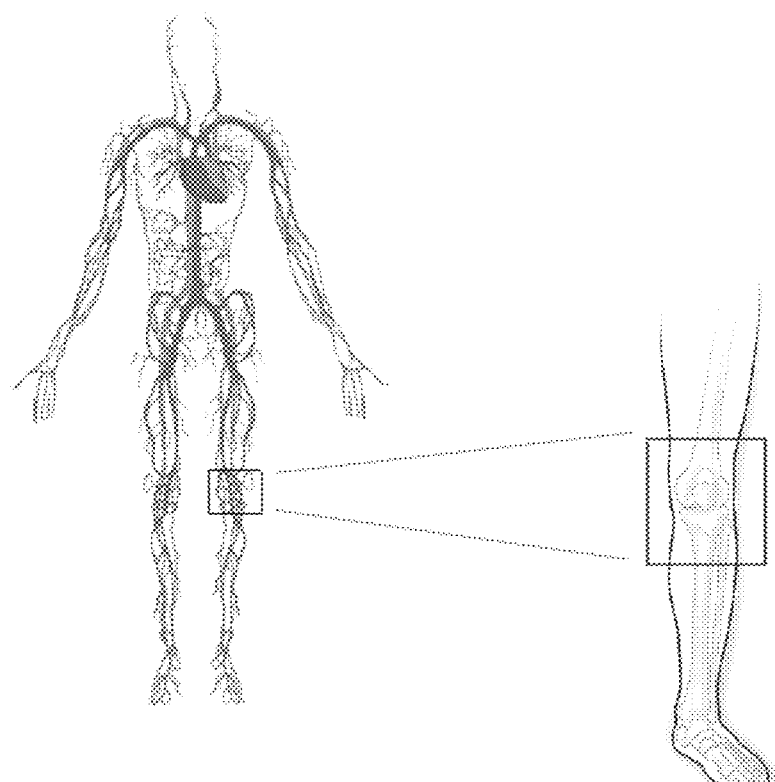
FIG. 12 depicts photon irradiation increases the effectiveness of bone growth medicine on the fractured bone.

FIG. 11 depicts a magnetic resonance (MR) image of a 50-year-old female patient with a trabecular fracture in the left knee necessitating swift bone growth. The arrow in the MR image indicates the location of the fracture. Treatment involved once a day subcutaneous injections of abaloparatide accompanied by red light and IR light irradiation. Remarkably, the fractured bone healed within 31 days with no surgical intervention for internal fixation was required. To expedite the healing process, the patient received subcutaneous injections of 80 micrograms (mcg) of abaloparatide once daily, together with red light and IR light irradiation directly on the fractured site, promoting ATP production and its conversion to cAMP. Red light and IR light photon irradiating on the knee selectively amplifies and increase the efficiency of bone growth for the fractured site, as depicted by FIG. 12.

Figure 13:
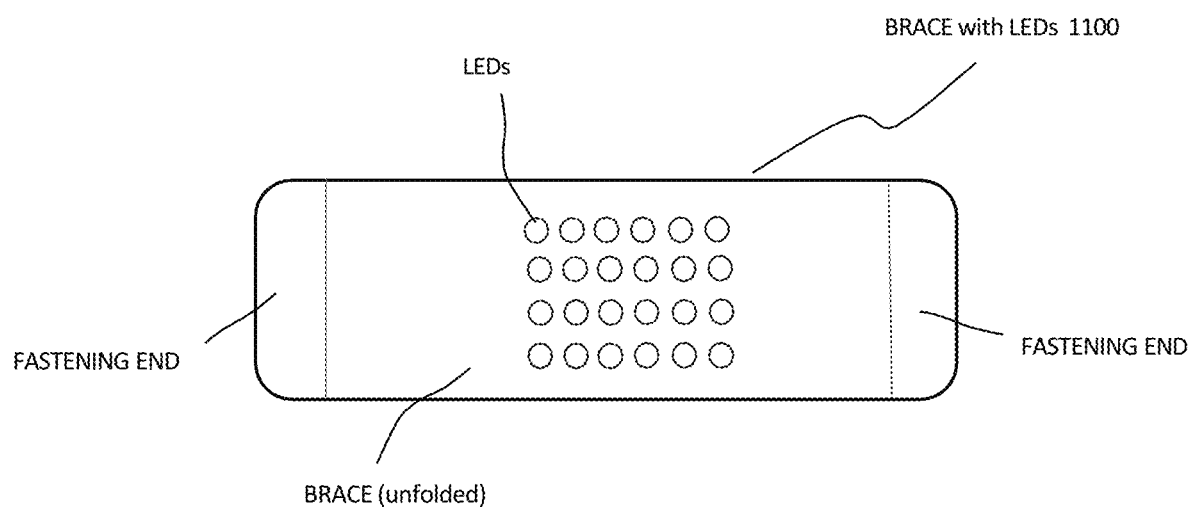
FIG. 13 depicts a brace with built-in LEDs.

The light therapy device 100 can be a handheld LED light device, as depicted in FIG. 1. Alternatively, the device can adopt the form factor of a brace 1100 with built-in LEDs, designed to attach to various parts of the body such as the neck, arm, elbow, hand, leg, knee, and feet, as shown in FIG. 13. This brace is constructed using flexible materials like fabrics or plastics to conform to joints, limbs, or specific body parts. It can be looped and fastened around, with mechanical fastening options at the ends using buckles, buttons, hook-and-loop (such as 'Velcro®'), and other mechanisms. Other form factors for the light therapy device include a band, waist belt, hat, glove, facial mask, clothing, etc., making it wearable. Additionally, the form factor can be a patch that attaches to the body. The device may feature a pouch for dispensing topical or inhalable medicines.

The wavelength of visible light is from approximately 380 nanometers (nm) to 750 nm. In the embodiments, light wavelength in the range of 630 nm to 750 nm is referred as "red" and light wavelength in the range of 750 nm to 1 m is referred as "infrared" (IR). Generally, infrared light can be further divided into three categories based on wavelength: near infrared from about 750 nm to 1,400 nm, mid infrared from about 1,400 nm to 3,000 nm, and far infrared from about 3,000 nm to 1 millimeter (mm). In one of the embodiments, the therapy device 100 may use red LEDs in the range of 630 nm to 750 nm and IR LEDs in the range of 750 nm to 1400 nm during treatment. One embodiment may use for red LEDs with a wavelength of approximately 660 nm and for IR LEDs with a wavelength of approximately 850 nm. In the human body, shorter-wavelength red light reaches shallower tissues while longer-wavelength IR reaches deeper tissues. The selection of different wavelength light-emitting diodes (LEDs) and the combined energy from red light and infrared (IR) light LEDs are determined by the intended use and the depth of the target organ and tissues. While a specific number and array of LEDs in device 100 have been disclosed, variations in quantity and layout can be employed in designs of different sizes, whether larger or smaller. LEDs with more than two wavelengths may also be used to cover a wider range of depths as needed. For instance, a combination of red LEDs, near-infrared LEDs, and mid-infrared LEDs may be utilized. It is noted that infrared (IR) light is invisible to the human eye. Therefore, combining IR with visible light also offers a safety benefit to the user, allowing them to know whether the light device is turned on.

The irradiation energy to the target area is in the range of approximately 30 to 150 joules per square centimeter ($J/cm^2$) treatment area and in a range of 10 to 30 minutes per session (or per day). The ratio of energy composition of red light and IR light is approximately 50%/50% of red light to infrared light. However, the ratio of red light and IR light composition can be optimized varying in ranges of up to 100%/0% or 0%/100% of red light to infrared light (i.e., 100% just red light or 100% just infrared light).

The red light and IR light irradiation amplifies target cell signaling through protein kinase A (PKA) activation to accelerate bone growth with intensified stimulation of osteoblasts. The administering PTHrP or PTH along with light irradiation can impact the outcome. The natural parathyroid hormone in human body follows a circadian rhythm characterized by a rise typically in late afternoon/early evening. The parathyroid hormone increases of calcium level in the blood, making it a preferable time for administering PTHrP (or PTH) accompanied by light irradiation for bone formation. Although the synthetic abaloparatide (or teriparatide) can be administered at any time of the day, an optimized time for administration is to coincide with the stimulated calcium levels.

The time interval between the injection of abaloparatide (or teriparatide) and the commencement of red light and IR light irradiation should be minimized, ideally less than 1 minute. However, a lapse time of up to 30 minutes should still be deemed preferable (i.e., the time to start treatment with the light after receipt of the medicine up to 30 minutes).

With the targeted application of red light and IR light irradiation on the fractured site, the therapeutic effect is specifically directed to the injured area, delivering an effective treatment for bone growth at the site of the fracture. Remarkably, the focused therapeutic approach facilitated the healing of the fractured knee within 31 days—a notably shorter duration compared to the typical healing time ranging from several months to years. It is noteworthy that the fractured bone healed without the need for surgery or implants. This example underscores the efficacy of combining abaloparatide, or teriparatide and/or red light and IR light irradiation to enhance local bone growth.

The method and system described above can be used for enhancing the bone growth in the treatment of osteoporosis either by PTH analogs (e.g., teriparatide) or PTHrP analogs (e.g., abaloparatide). However, it should be noted that PTHrP is not just limited to bones. It can influence the growth and specialization of cells in the different tissue, including cartilage cells (i.e., chondrocytes), muscle cells (i.e., myoblasts) and cells in the nervous system. The same method of applying red and IR photons can be used with the PTHrP to enhance the chondrogenesis and growth of cartilage in the joints. The cartilage is composed of cells known as chondrocytes, which maintain the extracellular matrix (ECM) and produce the cartilage matrix. Surrounded by collagenous fibers, chondrocytes release substances to make cartilage strong yet flexible. They are found within intervertebral discs and in any form of articular cartilage (AC), playing a crucial role in maintaining homeostasis within the acromioclavicular (AC) joints that provide cushioning in joint movements. The method of PTH or PTHrP with red light and IR light photon irradiation for stimulating cell growth can be used alone, or in combination with anti-inflammation DMARD therapies, for more effective treatment of connective tissue diseases such as Osteoarthritis (OA), Rheumatoid Arthritis (RA), Systemic Lupus Erythematosus (SLE), Scleroderma, Systemic Sclerosis, Sjôgren's Syndrome, Polymyositis, and etc. Furthermore, the method of PTH/PTHrP with red and IR light photon irradiation can also be used to stimulate muscle re-growth for treating Sarcopenia, an age-related disorder progressive loss of muscle mass and strength.

The foregoing description and embodiments have been presented for purposes of illustration and description and are not intended to be exhaustive or to limit the embodiments in any sense to the precise form disclosed. Also, many modifications and variations are possible in light of the above teaching. The embodiments were chosen and described to best explain the principles of the disclosure and its practical application to thereby enable others skilled in the art to best use the various embodiments disclosed herein and with various modifications suited to the particular use contemplated. The actual scope of the invention is to be defined by the claims.

Approximately: refers herein to a value that is almost correct or exact. For example, "approximately" may refer to a value that is within 1 to 10 percent of the exact (or desired) value. It should be noted, however, that the actual threshold value (or tolerance) may be application dependent. For example, in some embodiments, "approximately" may mean within 0.1% of some specified or desired value, while in various other embodiments, the threshold may be, for example, 2%, 3%, 5%, and so forth, as desired or as required by the particular application.

Configured To: various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits. Various components may be described as performing a task or tasks, for convenience in the description. Such descriptions should be interpreted as including the phrase "configured to." Reciting a component that is configured to perform one or more tasks is expressly intended not to invoke 35 U.S.C. § 112(f) interpretation for that component.

Although process (or method) steps may be described or claimed in a particular sequential order, such processes may be configured to work in different orders. In other words, any sequence or order of steps that may be explicitly described or claimed does not necessarily indicate a requirement that the steps be performed in that order unless specifically indicated. Further, some steps may be performed simultaneously despite being described or implied as occurring non-simultaneously (e.g., because one step is described after the other step) unless specifically indicated. Moreover, the illustration of a process by its depiction in a drawing does not imply that the illustrated process is exclusive of other variations and modifications thereto, does not imply that the illustrated process or any of its steps are necessary to the embodiment(s), and does not imply that the illustrated process is preferred.

Means Plus Function Language: to aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

Ranges: it should be noted that the recitation of ranges of values in this disclosure are merely intended to serve as a shorthand method of referring individually to each separate value falling within the range, unless otherwise indicated herein, and each separate value is incorporated into the specification as if it were individually recited herein. Therefore, any given numerical range shall include whole and fractions of numbers within the range. For example, the range "1 to 10" shall be interpreted to specifically include whole numbers between 1 and 10 (e.g., 1, 2, 3, . . . 9) and non-whole numbers (e.g., 1.1, 1.2, . . . 1.9).

What is claimed is:

1. A method of treating bone fracture comprising:
   administering parathyroid hormone-related protein (PTHrP) analog, abaloparatide, to bind with parathyroid hormone 1 receptors (PTH1R); and
   accompanied by applying light irradiation for a period of approximately 10 minutes to 30 minutes with a combination of predetermined energy levels locally to the fractured bone wherein one wavelength is in the range of 630 nanometers (nm) to 750 nanometers (nm), and another wavelength is in the range of 750 nanometers (nm) to 1400 nanometers (nm) to synergistically enhance the therapeutic effect of the abaloparatide on the bone fracture.

2. The method of claim 1, wherein the predetermined light irradiation is in the range of approximately 30 joules to 150 joules per square centimeter ($J/cm^2$) of a treatment area stimulating mitochondria to produce ATP in the cells of the bone.

3. The method of claim 1, wherein the PTHrP is administered by at least one of the group consisting of: subcutaneous injection, intravenous infusion, and topical application.

4. The method of claim 1, wherein the administering of the abaloparatide is accompanied by light irradiation is timed to coincide with stimulated calcium levels resulting from circadian rhythms.

5. A method of treating bone fracture comprising:
   administering parathyroid hormone-related protein (PTHrP) analog, abaloparatide, to bind with parathyroid hormone 1 receptors (PTH1R); and
   accompanied by applying light irradiation with a combination of predetermined energy levels locally to the fractured bone wherein one wavelength is in the range of 630 nanometers (nm) to 750 nanometers (nm), and another wavelength is in the range of 750 nanometers (nm) to 1400 nanometers (nm) wherein the predetermined light irradiation is in the range of approximately 30 joules to 150 joules per square centimeter ($J/cm^2$) of a treatment area to synergistically enhance the therapeutic effect of the abaloparatide.

6. The method of claim 5, wherein a predetermined time of light application per session is 10 minutes to 30 minutes stimulating mitochondria to produce ATP in the cells of the bone.

7. The method of claim 5, wherein the PTHrP is administered by at least one of the group consisting of: subcutaneous injection, intravenous infusion, and topical application.

8. The method of claim 5, wherein the administering of the abaloparatide is accompanied by light irradiation timed to coincide with stimulated calcium levels resulting from circadian rhythms.

9. A method of treating bone fracture comprising:
   administering parathyroid hormone-related protein (PTHrP) analog, abaloparatide, to bind with parathyroid hormone 1 receptors (PTH1R), wherein the administering of the abaloparatide is timed to coincide with stimulated calcium levels resulting from circadian rhythms; and
   accompanied by applying light irradiation with a combination of predetermined energy levels locally to the fractured bone wherein one wavelength is in the range of 630 nanometers (nm) to 750 nanometers (nm), and another wavelength is in the range of 750 nanometers (nm) to 1400 nanometers (nm) to synergistically enhance the therapeutic effect of the abaloparatide.

10. The method of claim 9, wherein the predetermined light irradiation is in the range of approximately 30 joules to 150 joules per square centimeter (J/cm$^2$) of a treatment area and a predetermined time of light application per session is 10 minutes to 30 minutes stimulating mitochondria to produce ATP in the cells of the bone.

11. The method of claim 9, wherein the PTHrP is administered by at least one of the group consisting of: subcutaneous injection, intravenous infusion, and topical application.

12. The method of claim 9, wherein a predetermined time of light application per session is 10 minutes to 30 minutes stimulating mitochondria to produce ATP in the cells of the bone.

13. The method of claim 9, wherein a predetermined light irradiation is in the range of approximately 30 joules to 150 joules per square centimeter (J/cm$^2$) of a treatment area.

14. The method of claim 9, wherein a predetermined time of light application per session is 10 minutes to 30 minutes stimulating mitochondria to produce ATP in the cells of the bone.

\* \* \* \* \*